(12) United States Patent
Gay et al.

(10) Patent No.: US 6,271,331 B1
(45) Date of Patent: Aug. 7, 2001

(54) FUNCTIONALIZED POLYORGANOSILOXANES AND ONE OF THE PROCESSES FOR THE PREPARATION THEREOF

(75) Inventors: Michel Gay, Villeurbanne; Philippe Jost, Taluyers; Michel Peignier, Lentilly; Christian Priou, Villeurbanne, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/454,879

(22) Filed: Dec. 3, 1999

Related U.S. Application Data

(62) Continuation of application No. 09/267,927, filed on Mar. 9, 1999, now Pat. No. 6,140,447, which is a continuation of application No. 08/836,510, filed as application No. PCT/FR95/01504 on Nov. 15, 1995, now abandoned.

(30) Foreign Application Priority Data

Nov. 18, 1994 (FR) .................................. 94 14056

(51) Int. Cl.$^7$ .................................................. C08G 77/08
(52) U.S. Cl. ................................ 528/15; 528/25; 528/29; 556/427; 556/428; 556/429; 556/451; 556/453; 556/457
(58) Field of Search .................................. 528/15, 25.29; 556/427, 428, 429, 451, 453, 457

(56) References Cited

U.S. PATENT DOCUMENTS

| | | | |
|---|---|---|---|
| 5,037,878 | 8/1991 | Cerles | 524/588 |
| 5,310,842 | 5/1994 | Ichinohe | 528/12 |
| 5,420,222 | 5/1995 | Stepp | 528/31 |
| 6,140,447 | * 10/2000 | Gay et al. | 528/15 |

FOREIGN PATENT DOCUMENTS

| | | | |
|---|---|---|---|
| 0 421 588 | 4/1991 | (EP) | C08F/283/12 |
| 0 565 327 | 10/1993 | (EP) | C09D/183/06 |

* cited by examiner

Primary Examiner—Margaret G. Moore
(74) Attorney, Agent, or Firm—Jean-Louis Seugnet

(57) ABSTRACT

The present invention relates to multifunctionalized alkoxy, the alkoxy functionality Y being introduced onto a suitable polyhydroorganosiloxane by a dehydrogenation/condensation reaction from the alcohol from which Y derives and then the functionality W by a hydrosilylation reaction from the olefinic compound form which W derives. The multifunctionalized alkoxy polyorganosiloxanes can be used as antiadhesion modulators in silicone compositions and as silica covering agents in silicone compositions containing fillers.

6 Claims, No Drawings

FUNCTIONALIZED POLYORGANOSILOXANES AND ONE OF THE PROCESSES FOR THE PREPARATION THEREOF

This application is a Continuation application of U.S. application Ser. No. 09/267,927, filed Mar. 3, 1999 now U.S. Pat. No. 6,140,447 which is a Continuation application of U.S. application Ser. No. 08/836,510, filed on Jul. 14, 1997, now abandoned, which is an application under 35 U.S.C. Section 371 of International Application Number PCT/FR95/01504, filed Nov. 15, 1995.

The field of the present invention is that of polyorganosiloxanes containing a number of functionalities introduced by substituents of the silicon and conferring specific properties on silicone polymers, for example antiadhesion, lubricating or reinforcing properties, which are much sought after in silicone applications.

More precisely, the present invention relates to a multi-functionalized polyorganosiloxane in which the functionalities are each carried by different siloxy units, via an SiC or SiOC bond.

The present invention also relates to a process for the functionalization of polyorganosiloxanes which make it possible, in particular, to result in the multifunctionalized polyorganosiloxanes targeted above.

The functionalization of the polyorganosiloxanes can conventionally be carried out by substitution of the hydrogens carried by the silicon atoms of the chain.

According to a first route, this substitution can consist of a hydrosilylation reaction between a polyorganohydrosiloxane and an olefinic reagent carrying at least one π double bond capable of reacting with the hydrogen according to an addition mechanism. Hydrosilylation is a reaction which is fully know in the technical field under consideration. This reaction is usually catalysed with platinum. It is widely described in the literature. In this respect, reference may be made, for example, to the article by V. M. Kopilov et at., Z. Obsh. Khim., vol. 57 (5), (1987) p. 1117–1127. In this first route, all the silicon atoms containing available hydrogen are substituted by organic units via SiC bonds, the said organic units being introduced by the olefin reactant(s). One illustration, among others, of hydrosilylation is given in European Patent Application No. 504,800, which described the addition of a polyoxyalkylene substituted by an olefin group (vinyl) to a polydimethylhydrosiloxane of formula:

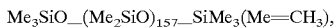

$Me_3SiO-(Me_2SiO)_{157}-SiMe_3(Me=CH_3)$, in the presence of a monocarboxylic ester of a solvent of the alkanediol type. In this case, it clearly seems that single type of functionalization can be envisaged and only the groups capable of being substituted by olefin residues can be grafted onto the polyorganosiloxane.

A second functionalization route is that according to which the silicons of the polyorganosiloxane concerned are substituted by functional residues bonded to the polyorganosiloxane by virtue of SiOC bridges. The reactions which can be envisaged for doing this are, for example, those involving α, ω-chlorosiloxanes and alcohols or alternatively polyorganohydrosiloxanes and alcohols according to a dehydrogenation/condensation mechanism.

These dehydrogenation/condensation reactions, also described as alcoholyses of organohydropolysiloxanes, are described in particular in S. Koama and Y. Humeki, Journal of Applied Polymer Science, Vol. 21 (277), pages 863–867.

This article refers to polymethylhydrosiloxanes brought into contact with an alcohol of the methanol or ethanol type and with a catalyst chosen from bases and certain metal chlorides (Lewis acids). The solvent employed is benzene. The writers thus obtain a polyalkoxymethylsiloxane which itself also has only one functionality.

Resources has also been and to dehydrogenation/condensation in the invention described by U.S. Pat. No. 5,310,842 relating to alkoxy-substituted polyorganosiloxanes. These products comprise dimethylsiloxy and methylalkoxysiloxy units and contain from 4 to 30 carbon atoms. The catalyst employed in this dehydrogenation/condensation is platinum-containing in nature (chloroplatinic acid). All the starting methylhydrosiloxy functionalities are converted (degree of conversion greater than 99%) to alkoxy-substituted units. The alkoxylated side chains are involved in the compatibilization of the polyorganosiloxanes with other products such as, for example, organic polymers, with which they are used in the final applications. Although the writers maintain that these alkoxylated polyorganosiloxanes have good resistance to hydrolysis, it may be permitted to doubt this, taking into account the not insignificant sensitivity of the oxygen bridge in this respect. In addition, this prior invention retains the disadvantage of the monofunctionalization of the polyorganosiloxanes.

This review of the prior art makes it appear that multi-functionalities polyorganosiloxanes are lacking. Such products would nevertheless be highly appreciable in certain uses of silicones, because it is obvious that the multifunctionalization only causes an increase in the potentialities of these products which are already very wide-ranging. The introduction of multiple functionalities by grafting would also provide the undeniable advantage of making it possible to construct silicones to measure, specifically suited to the targeted applications.

In the light of this irrefutable fact, one of the essential objects of the present invention is to provide a functionalities polyorganosiloxanes, in particular a multifunctionalized polyorganosiloxane, and more particularly still a polyorganosiloxane comprising at least two siloxy sites (or units) of different functionalization, each carrying one type of functionality, corresponding to a plurality of functional types.

Another essential object of the invention is to provide a polyorganosiloxanes which can be obtained simply and economically.

Another essential object of the invention is to provide a process for the preparation of polyorganosiloxanes having simultaneously a number of types of functional groups introduced by grafting, in particular two types of functional groups, it being necessary of the said process to be easy to implement and with a low cost price, both as regards the raw materials employed and as regards the equipment, energy and time required.

In seeking to meet these objectives, the Applicant Company has discovered in an entirely surprising and unexpected way, after many studies and experiments, that, in contrast to what is taught by Koama and Humeki, the alcoholysis of polymethylhydrosiloxanes results, under certain conditions, in alkoxy-substituted siloxy units and in hydrosiloxy units in which the hydrogen has not reacted, according to a specific stoichiometry.

It follows that the present invention, which makes it possible to achieve the abovesaid objectives among other, relates, as new product per se, to a functionalized polyorganosiloxanes, and more particularly a multifunctionalized polyorganosiloxane, comprising, per molecule, -α- on the one hand, at least one functional siloxy unit of formula:

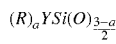 (I)

in which
  *a=0, 1 or 2
  *R is a monovalent hydrocarbon radical chosen from linear or branched alkyls having from 1 to 6 atoms, in particular methyl, ethyl, propyl or butyl, and/or from aryls and in particular phenyl, methyl being more particularly preferred, the R radicals being identical or different when a=2,
  *Y is a linear or branched alkoxy radical preferably chosen from $C_1$–$C_{15}$ alkoxys, in particular $C_1$–$C_6$ alkoxys, methoxy, ethoxy and (iso)proxy being more particularly used,
  -β- and, on the other hand, at least one functional siloxy unit of formula:

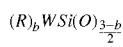 (II)

in which
  *b =0, 1 or 2,
  *R corresponds to the same definition as that given above for the R substituents of the unit (I) and can be identical to or different form the latter,
  *W is a monovalent hydrocarbon radical having from 2 to 30 carbon atoms and optionally S and/or O atoms and constituting a functional residue, bonded to the silicon via an Si–C bond,
    this residue being chosen form the following groups:
    (i) a linear or branched alkyl group comprising at least 7 carbon atoms,
    (2i) a linear or branched $C_2$–$C_{20}$ alkenyl group containing one or a number of double bonds in and/or at the chain end(s), the said double bonds preferably being conjugated and/or combined with at least one activating group situated at the α-position and advantageously consisting of an ether or a thioether,
    (3i) an unsaturated aliphatic mono- or bicyclic group containing 5 to 20 cyclic carbon atoms and one or two ethylenic double bond(s) in the ring optionally substituted by one or two linear or branched $C_1$–$C_3$ alkyl group(s), the said cyclic group optionally being bonded to the silicon via a linear or branched $C_2$–$C_{10}$ alkylene radical,
    (4i) a mercaptoalkyl group of formula

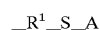 (4i)

in which
  *$R^1$ represents a linear or branched $C_2$–$C_{10}$ alkylene radical, optionally comprising at least one oxygen heteroatom, or an alkylenencycloalkylene radical in which the alkylene part has the same definition as that given immediately above and the cyclic part contains 5 to 10 carbon atoms and is optionally substituted by one or two linear or branched $C_1$–$C_3$ alkyl group(s),
  *A corresponds:
    →either to hydrogen,
    →or to a masking group M bonded to S via a bond which is labile under given conditions and which makes possible the replacement of M by H or the creation of an active species —$R^1$—SO;
  (5i) a group comprising a polysulphide entity and corresponding to the following formula:

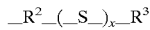 (5i)

with
  *x=1 to 6,
  *$R^2$ having the definition as $R^1$ above,
  *$R^3$ is a linear or branched $C_1$–$C_{10}$ alkyl,
  (6i) a group containing at least one ring, at least one of the elements of which is a sulphur atom, and corresponding to the formulae below:

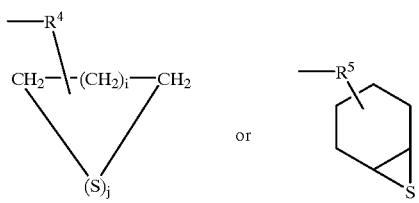

in which
  *i=0, 1 or 2 and j=1 to 6
  *the substituents $R^4$ and $R^5$ are divalent radicals as defined above for $R^1$,
  (7i) a sulphoxide group of formula:

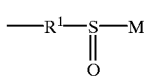 (7i)

in which the symbols $R^1$ and M have the definitions given above for the formula (4i);
  -γ- and, optionally, at least one siloxy unit (III) of following formula:

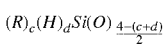 (III)

in which
  *c=0, 1, 2 or 3 , d=0 or 1 and c+d≦3
  * the R substituents being as defined above in the units (I) and (II).

To the knowledge of the Applicant Company, no document of the prior art describes polyorganosiloxanes having at the same time units functionalized by a functional residue bonded to the silicon bias an SiOC bond and siloxy units functionalized by a functional residue bonded to the silicon via an SiC bond.

In this polyorganosiloxanes according to the invention, the first alkoxy functionality Y is carried by the units of formula (I), whereas the second hydrocarbon functionality W appears in the units of formula (II) defined above.

According to the usual terminology in silicones, these units (I) and (II) can be M, D but also T units. The presence of T units corresponds to an alternative form in which the polyorganosiloxanes exist in the form of linear chains crosslinked to one another.

The Y functional groups are characterized in that they can be hydrolysed and in that they can therefore make it possible to grant onto various substrates, which can be particularly advantageous in certain applications.

W can consist of a hydrocarbon functional group which is more difficult to hydrolysed and which is capable of expressing various properties according to its chemical nature. This can be the compatibilization with organic polymers or alternatively the introduction of a crosslinking function group into the polyorganosiloxane.

In accordance with an advantageous form of the invention, this functional substituent W is chosen from the following radicals:

an alkyl radical (i) comprising from 8 to 30 carbon atoms and preferably chosen from the following alkyl radicals: octyl, dodecyl, undecyl or tridecyl;

a $C_6$–$C_{10}$ radical (2i) containing a double bond and optionally another conjugated with the first, the said radical advantageously being hexenyl or dodecenyl;

a $C_5$–$C_6$ monocyclic radical (3i), preferably cyclohexenyl or 1-methylcyclohex-1-enyl, optionally bonded to the silicon via a linear or branched $C_2$–$C_6$ alkylene radical, preferably —$CH_2$—$CH_2$—, —$CH_2$—$CH(CH_3)$— or —$(CH_2)_3$—;

a radical (4i), in the formula of which $R^1$ is a $C_2$–$C_{10}$ alkylene optionally comprising ester and/or ether functional groups, the said radical (4i) preferably being selected from the following list:

—$CH_2$—$CH_2$—⟨cyclohexyl⟩—S—A;

—$CH_2$—$CH$(CH_3)—⟨cyclohexyl⟩(S—A)(CH_3)$;

—$(CH_2)_3$—O—C(=O)—$(CH_2)_2$—S—A;

—$(CH_3)_3$—O—$(CH_3)_3$—S—A:

with A=H or M
the preferred M groups being:

$*M = $ —C(=O)—D with D corresponding to a $C_1$–$C_{12}$ hydrocarbon radical optionally comprising at least one heteroatom, the more particularly preferred D radicals being phenyl, phenylamino, $C_1$–$C_3$ alkyl and —S—phenyl, $*M=$—$R^6$—$R^7$, with $R^6$ corresponding to a linear or branched $C_1$–$C_6$ (advantageously $C_2$) alkylene and $R^7$:

to a linear or branched $C_1$–$C_4$ (advantageously $C_1$) alkyl, to a linear or branched $C_1$–$C_3$ advantageously $C_1$) alkoxy, to a phenyl radical, to an alkoxysilyl of formula —$Si(R')_k(OR')_{3-k}$, where the R' symbols, which are identical or different, are linear or branched $C_1$–$C_3$ (preferably $C_2$) alkyl radicals and k=0, 1, 2 or 3, the trialkoxysilyl (then k=0) being more particularly preferred, or to a radical of formula —C(=O)—$R^8$   or   —C(=O)—$OR^8$ with $R^8$=linear or branched $C_1$–$C_3$ alkyl, $*M = $ —C—[⟨phenyl⟩]$_3$.

$*M=$—$Si(R'')_l(OR'')_{3-l}$, where the R'' symbols, which are identical or different, are linear or branched $C_1$–$C_3$ (preferably $C_2$) alkyl radicals and l=0, 1, 2 or 3, the trialkoxysilyl (then l=0) being more particularly preferred, a radical (5i) of formula:
$(CH_2)_3$—$(S)_4$—$(CH_2)_2$—$CH_3$ a radical (6i) of formula:

—$(CH_2)_3$—O—$CH_2$—⟨epoxide⟩;    ⟨tetrahydrofuran⟩—$CH_2CH_2$—;

—$(CH_2)_2$—⟨cyclohexyl-S⟩   or   ⟨dithiolane⟩—$CH_2CH_2$— a radical (7i) of formula:

—$CH_2$—$CH_2$—⟨cyclohexyl⟩(S—M)(O)

where the symbol M represents one of the preferred groups mentioned above with respect to the radical (4i).

As indicated above, the invention is not limited to the case where the polyorganosiloxane contains only two types of functionality Y and W. Indeed, according to an advantageous alternative form, the polyorganosiloxanes contains, in addition to the units (I) and (II), at least one unit (III).

These units (III) of SiH type are, for example, residual siloxy sites in which the hydrogen has not reached in order to be substituted by Y or W. This residual hydrogenated nature can prove to be useful in certain applications of polyorganosiloxanes according to the invention.

It should be emphasized that from the moment that a unit of a given type (I, II or III, e.g.) is present in the polyorganosiloxane in more than one example, the various examples can be identical to or different from one another.

Taking into account the values which the indices a to d attributed to the substituents in the units (I), (II), (III) can take, it should be understood that the polyorganosiloxanes according to the invention can have a linear and/or branched and/or cyclic structure.

The preferred R radicals are: methyl, ethyl, n-propyl, isopropyl or n-butyl, preferably methyl. More preferentially still, at least 80% by number of the R radicals are methyls.

The preferred alkoxy radicals Y are the ethoxy radicals.

In order to be even more specific as regards the polyorganosiloxanes to which the invention relates, as new products, mention is first of all made of those formed by statistical, sequenced or block linear copolymers of following average formula:

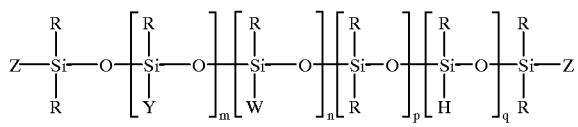

(IV)

in which:
the symbols Y, W and R are as defined above,
the symbol Z is a monovalent radical chosen from the radicals formed by hydrogen and from those corresponding to the definitions of R, Y and W,
the sum $m+n+p+q \geq 3$, preferably between 3 and 100; the scenario in which $p=q=0$, $m \geq 1$ and $n \leq 50$ being more particularly preferred,
$0 \leq m \leq 100$, preferably $1 \leq m \leq 50$
$0 \leq n \leq 100$, preferably $1 \leq n \leq 50$
$0 \leq p \leq 20$, preferably $0 \leq p \leq 10$
$0 \leq q \leq 40$, preferably $0 \leq q \leq 20$
with the conditions according to which:
if $m=0$, at least one of the Z substituents corresponds to a radical corresponding to the definition characterizing Y,
if $n=0$, at least one of the Z substituents corresponds to a radical corresponding to the definition characterizing W,
and if $m=n=0$ and $p+q \geq 1$, then one of the Z substituents corresponds to a radical corresponding to the definition characterizing Y and the other of the Z substituents corresponding to the definition characterizing W.

Mention may be made, among the more particularly preferred polyorganosiloxanes of formula (IV), of those in which $p=q=0$ and $0.1 \leq m/n \leq 5$, preferably $1 \leq m/n \leq 5$ and more preferentially $1.5 \leq m/n \leq 3$.

An alternative to the linear structure of the polymers of formula (IV) defined above relates to the polyorganosiloxanes consisting of cyclic copolymers of following average formula:

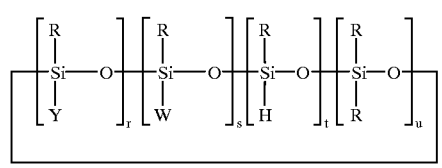

(V)

in which Y, W and R are as defined above,
and with r, s, t and u representing positive whole or decimal numbers:
+the sum $r+s+t+u \geq 3$, preferably between 3 and 8, the scenario in which $t=u=0$ being more particularly preferred,
+$1 \leq r \leq 8$, preferably $1 \leq r \leq 4$
+$1 \leq s \leq 8$, preferably $1 \leq s \leq 4$
+$0 \leq t \leq 8$, preferably $0 \leq t \leq 4$
+$0 \leq u \leq 8$, preferably $0 \leq u \leq 4$.

The polyorganosiloxanes according to the invention preferably consist of the products corresponding to those in which $R=CH_3$ and $p=u=0$ in the formulae (IV) and (V) defined above.

It is obvious that in these formulae (IV) and (V), as already indicated above, the W radicals can be identical or different in nature when $n>1$ and $s>1$.

The mixtures of polyorganosiloxanes of the type of those defined above come within the context of the present invention.

According to another of its aspects, this invention is targeted at a process for the preparation of functionalized polyorganosiloxanes, in particular multifunctionalized polyorganosiloxanes, which can in particular be those described above.

This functionalization process advantageously consists essentially, on the one hand, in reacting
a starting polyorganosiloxane comprising units of formula (II) as defined above, in which W represents hydrogen,
with at least one alcohol from which the functionality Y of the unit (I) derives, and which is useful both as reactant and as reaction solvent, in the presence of a catalyst, at least one of the active elements of which is chosen from the transition metals, according to a dehydrogenation/condensation mechanism (1st stage),
and, on the other hand, in carrying out the addition of the polyorganosiloxane which has been converted by dehydrogenation/condensation to at least one olefinic compound, from which the functionality W of the unit (II) derives, according to a hydrosilylation mechanism (2nd stage), in the presence of a catalyst and preferably at a temperature of between 5 and 100° C. and more preferentially still between 20 and 90° C.

One of the novel features of this process lies in the use of the alcohol corresponding to the Y group, both as reactant and as reaction solvent in the dehydrogenation/condensation stage. This is one of the essential differences from the known alcoholysis method according to Koama and Humeki. In accordance with the invention, it was possible to observe that, whatever the amount of alcohol used in the process, it is not possible to convert all the SiW groups with W=H of the starting polyorganosiloxane. Thus, after a certain limit degree of conversion, which varies according to the reaction conditions, the stoichiometry and the nature of the reactants, the residual SiH groups become inactive with respect to dehydrogenation/condensation. For example, in the presence of ethanol, the degree of conversion of the initial SiH functional groups levels out at 66%.

This novel dehydrogenation/condensation therefore results in a polyorganosiloxane containing at least one related functionality and free SiH functional groups and allowing access to the multifunctional polyorganosiloxane, as described in the following.

The alcohols employed are preferably linear or branched monohydroxylated alkanols (primary, secondary or tertiary alkanols, preferably primary alkanols) preferably chosen from the following list: methanol, ethanol, (iso)propanol or (n-)butanol, ethanol being preferred.

As regards the catalyst, it is advantageously chosen from those containing at least one of the following elements: Pt, Rh, Ru, Pd, Ni and their combinations, this catalyst optionally being coupled to a support, which may or may not be inert.

According to a preferred arrangement of the invention, the catalyst is taken from the family of the platinum catalysts conventionally used for carrying out hydrosilylation reactions. These platinum catalysts are fully described in the literature. Mention may in particular be made of the complexes of platinum and of an organic product described in U.S. Pat. No. 3,159,601, U.S. Pat. No. 3,159,602 and U.S. Pat. No. 3,220,972 and European Patents EP-A-57,459, EP-188,978 and EP-A-190,530 and of the complexes of platinum and of vinylated organopolysiloxane described in U.S. Pat. No. 3,419,593, U.S. Pat. No. 3,715,334, U.S. Pat. No. 3,377,432 and U.S. Pat. No. 3,814,730. The Karstedt catalyst is an example of a platinum catalyst which is suitable for the process according to the invention (U.S. Pat. No. 3,775,452, Karstedt).

The nickel-based catalysts, such as for example Raney nickel, are a possible alternative to the platinum catalysts.

As regards the reaction conditions, the dehydrogenation/condensation can be carried out over a wide temperature range extending, for example, from 0 to 200° C., but it is clear that it is preferable to carry it out at a temperature between 20 and 80° C. and preferably between 40 and 70° C.

The second stage of the process according to the invention consists of an addition reaction of the intermediate hydrogenated polyorganosiloxane, produced by dehydrogenation/condensation, to at least one olefinic compound carrying at least one π bond.

It concerns a hydrosilylation mechanism, in the presence of a catalyst and, preferably, at a temperature of between 5 and 100° C. and more preferentially still between 20 and 90° C.

According to preferred methodology, the hydrosilylation is initiated by adding the olefinic compound, from which the W radical as defined above derives, to the intermediate alkoxylated polyorganosiloxane, once the dehydrogenation/condensation has been completed. In practice, this addition can taken place when hydrogen evolution has ceased.

The reactive alkene can be formed by a mixture of products containing just one or a number of precursor types of W radicals, which determine the multifunctionality of the final polyortganosiloxane. In the case in which a number of W types are provided, the alkene corresponding to the second functionality is preferably allowed to react first, then, once this alkene has completely reacted, the alkene corresponding to the third functionality is incorporated, and so on.

Instead of being incorporated in the reaction mixture after the deyhydrogenation/condensation, the olefinic compound which is a precursor of W can be used before beginning this first stage of the process, or alternatively during the latter.

According to a preferred characteristic of the invention, it is arranged for the hydrosilylation to be catalysed by at least a part of the dehydrogenation/condensation catalyst and preferably exclusively by this catalyst.

This is one of the particularly advantageous and unexpected aspects of the process of the invention. Indeed, it is entirely surprising to observe that the dehydrogenation/condensation catalyst, preferably of platinum nature, is still active in this second hydrosilylation stage.

Indeed, it is certainly known that the catalyst experiences a degree of deterioration in its performance during dehydrogenation/condensation. However, what is still more surprising is that the catalyst is present in the post-dehydrogenation/condensation medium containing the polyorganosiloxanes carrying residual SiH groups. Now, in theory and according to a prejudice which is widespread in the field under consideration, the hydrosilylation catalyst, in particular a platinum catalyst, is only active if it is first brought into the presence of the reactive product comprising at least one π bond, so that the formation of an inactive colloid ought to have been observed in the case of the invention. However, none is observed.

In contrast, the residual SiH groups are particularly reactive, with respect to olefinic compounds added, by virtue of the effect of the hydrosilylation catalyst, which is itself also entirely effective. This result makes it possible to obtain, in a single sequence and without changing the reactor, a polyorganosiloxane containing a number of different functionalities.

The olefinic compounds used can be easily deduced from the definition of W given above. The choice as regards this radical is determined by the targeted applications (one or a number of different functionalities).

The hydrosilylation stage can advantageously take place at room temperature and in bulk or in solution, for example in the alcohol which was used as solvent and as reactant in the dehydrogenation/condensation reaction.

At the end of the reactions, the crude polyorganosiloxanes which are obtained can be purified, in particular by passing through a column filled with an ion exchange resin and/or by simple evaporation of the excess reactants introduced and optionally of the solvent used by heating between 100 and 180° C. under reduced pressure.

The starting polyorganosiloxane is advantageously selected from those corresponding to the following formula:

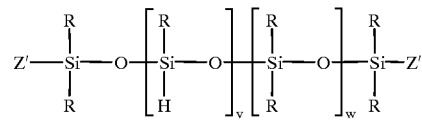

(VI)

in which:
the R symbols are identical or different and are as defined above in the legend to the formula of the units (I) and (II), the Z' symbols are identical or different and correspond to R or to hydrogen, v is an integer or a decimal≧0 definable as follows: v=n+m+q; n, m and q corresponding to the definitions given above in the legend to the formula (IV), with the condition according to which, if v=0, then w≧1 and the two Z' radicals correspond to hydrogen, w corresponds to the same definition as that of p given above in the legend to the formula (IV).

The starting polyorganosiloxanes which are used, for example, in the preparation of the cyclic functionalized products are those selected from those corresponding to the following average formula:

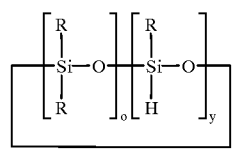

(VII)

in which:
the R symbols are identical or different and are as defined above in the legend to the formula of the units (I) and (II), o corresponds to the same definition as that of u given above in the legend to the formula (V), y is an integer or a decimal≧0 definable as follows: y=r+s+t and y+u≧3, r, s, t and u corresponding to the definitions given above in the legend to the formula (V).

According to another of its aspects, the present invention relates to the application of the polyorganosiloxanes defined above, and of those obtained by the process which is also described above, as antiadhesion modulators and/or crosslinking agents in silicone compositions. These polyorganosiloxanes can also be advantageously used, and in that case it is a preferred mode of application, as covering agents for siliceous fillers, for the purpose of promoting the use of the silica in silicone elastomer compositions and of making it possible to reinforce the silicone elastomer products obtained from these compositions, such as, for example, sealing and weather-stripping mastics and protective coatings used in the building industry.

The present invention will be better understood in the light of the examples which follow and which describe the various multifunctionalized polyorganosiloxanes and the process for the preparation thereof. Other advantages and alternative implemental forms of the invention will also emerge from these examples.

EXAMPLES

I—1st Stage of the Process According to the Invention

Example 1

Preparation of a First Polyorganosiloxane (POS) Containing Si—OEt and Si—H Functionalities 300 ml of ethanol, dried beforehand over 3 angstrom molecular sieve, and 10 μl of Karstedt catalyst (10% in hexane) are charged, under a nitrogen atmosphere, to a 500 ml, three-necked, round-bottomed flask equipped with a mechanical stirrer, a thermometer and a dropping funnel. The mixture is stirred at 65° C. and the dropwise addition of polymethylhydrosiloxane (40 g, $dp_n$=50) is begun. Significant hydrogen evolution is observed The rate of addition of the Si—H fluid is adjusted in order to control the hydrogen flow and the exothermicity of the reaction. At the end of the addition, the mixture is left stirring for one hour. The excess ethanol is removed using a rotary evaporator. A clear and colourless oil is recovered, with a viscosity of 52 mPa.s, corresponding to the following average formula according to an NMR analysis:

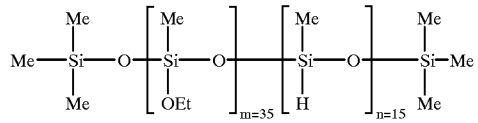

This oil exhibits very good stability on storage with moisture excluded.

Example 2

Preparation of a Second Precursor POS Containing Si—OEt and Si—H

The reactants and the procedure are the same as in Example 1. The product obtained corresponds to the same formula, apart from the difference that m=32 and n=18.

II—1 and 2nd Stages of the Process According to the Invention

Example 3

Preparation of a POS Containing Si—OEt and Si—Octyl Functionalities

The preparation is carried out as in Example 1 but, instead of evaporating the excess alcohol, 36 g of 1-octene are run in dropwise. After addition, the reaction mixture is heated at 60° C. until all the Si—H functional groups have been consumed. The excess alcohol and octene are then evaporated off. 80 g of clear and slightly coloured oil are recovered. NMR analysis reveals the following structure (NMR):

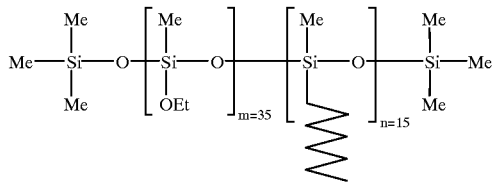

Example 4

Preparation of Another POS Containing Si—OEt and Si—Octly Functionalities

The reactants and the procedure are identical to those in Example 3, but starting with the POS precursor containing Si—OEt and Si—H of Example 2. The POS corresponds to the same formula, apart from the difference that m=32 and n=18.

Example 5

Preparation of a POS Containing Si—OEt and Si—hexenyl Functionalities

The preparation is carried out as in Example 3, the octene being replaced with 1,5-hexadiene.

The amounts of SiOEt/SiH POS and of hexadiene used are 100 g and 122.81 g respectively per 14 mg of initial [Pt].

The temperature of the reaction mixture is maintained at =30° C.

At the end of the handling operation, a clear and slightly coloured oil is recovered.

NMR reveals the following formula:

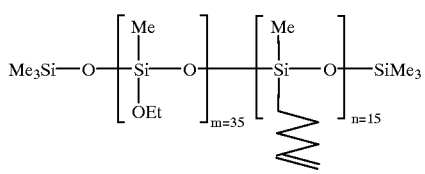

Example 6

Preparation of a POS Containing Si—OEt and Si—vinylcyclohexenyl Functionalities 6.1—Synthesis of the POS The preparation is carried out as in Example 3, but the octene is replaced with 4-vinyl-1-cyclohexene (VCH).

The amounts of reactants used are the following:

| | |
|---|---|
| SiOEt/SiH POS = | 100 g |
| VCH = | 39.16 g |
| Initial Karstedt Pt = | 10 mg. |

The temperature of the reaction mixture is maintained at =80–85° C.

130 g of a clear, slightly yellowed oil are recovered, with the formula:

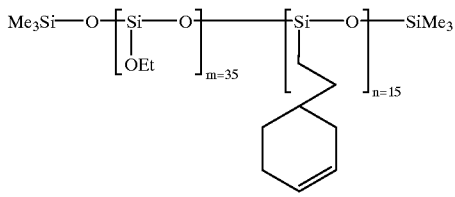

6.1—Use of the POS as Covering Agent

The oil prepared in Example 6.1 is used as follows in a composition intended for the preparation of a silicone elastomer containing a siliceous filler:

Approximately 1 liter of each of the two compositions, the constituents of which, expressed in parts by weight, are indicated in the following table, is prepared in a 3 liter reactor equipped with a three-bladed central stirrer:

| Compositions | Control | Example 6.2 |
| --- | --- | --- |
| 48 V 135,000 Oil (1) | 110 | 110 |
| 47 V 1,000 Oil (2) | 20 | 20 |
| POS of Example 6.1 | 0 | 1 |
| VTMS (3) | 5 | 5 |
| Accelerator A (4) | 0.64 | 0.64 |
| Aerosil 150' (5) | 10 | 10 |
| Silane 1411' (6) | 1.2 | 1.2 |
| Breox B 225' (7) | 0.75 | 0 |
| Catalyst B (8) | 0.1 | 0.1 |

(1) α,ω-Bishydroxypolydimethylsiloxane oil with a viscosity equal to 135,000 mPa · s at 25° C.
(2) α,ω-Bis(trimethylsiloxy)polydimethylsiloxane oil with a viscosity equal to 1,000 mPa · s at 25° C.
(3) Vinyltrimethoxysilane crosslinking agent.
(4) 4% by weight solution of LiOH · H$_2$O in methanol.
(5) Pyrogenic silica with a density of 150 ± 30 m$^2$/g, marketed by Degussa.
(6) Silane of formula

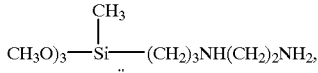

marketed by Hüls.
(7) Polypropylene/polyethylene glycol containing 1% by weight of OH groups, marketed by BP Chemical.
(8) 50/50 mixture by weight of dibutyltin dilaurate and of dibutyltin diacetylacetonate chelate.

Each composition is prepared in the following way:

| Operation | Stirring | Duration |
| --- | --- | --- |
| 1. Charging 48 V 135,000 and 47 V 1,000 oils, VTMS and the POS of Example 6.1, then | — | — |
| 2. Stirring at 25° C., then | 250 rev/min | 2 min |
| 3. Adding Accelerator A with reducing stirring, then | 100 rev/min | — |
| 4. Stirring, then | 350 rev/min | 4 min |
| 5. Adding the silica, after having halted the stirring, then | — | — |
| 6. Mixing with stirring, then | 350 rev/min | 4 min |
| 7. Adding the ingredients Silane 1411, Breox and Catalyst B with reduced stirring, then | 100 rev/min | — |
| 8. Mixing with stirring, then | 350 rev/min | 4 min |
| 9. Placing under a reduced pressure of 46.6 × 10$^2$ Pa | — | 6 min |

Subsequently, after preparation each composition is spread with a coating knife so as to produce a film with a thickness of 2 mm which is left to crosslink for 4 days at 250° C.

The following mechanical properties are measured on the dried films:
- the Shore A hardness (SAH) at 7 days and at 14 days according to ISO standard 868,
- the tensile strength (TS) in MPa according to AFNOR-T standard 46002,
- the elongation at break (EB) in % according to AFNOR-T standard 46002, and
- the elastic modulus (M100) at 100% of elongation according to AFNOR-T standard 46002, in MPa.

The mechanical properties TS, EB and M100 are the initial properties measured after 4 days.

The results are combined in the following table:

| Compositions | Control | Example 6.2 |
| --- | --- | --- |
| SAH 7 days | 17 | 20 |
| SAH 14 days | 17 | 21 |
| TS | 1.1 | 1.1 |
| EB | 540 | 480 |
| M100 | 0.34 | 0.39 |

What is claimed is:
1. A process for the preparation of a statistical, sequenced or block linear polyorganosiloxane copolymer of following average formula:

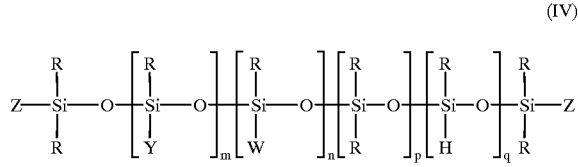

(IV)

wherein:

Y is methoxy, ethoxy, propoxy or isopropoxy;

R is a monovalent hydrocarbon radical chosen from linear or branched alkyl having from 1 to 6 atoms;

W is a monovalent hydrocarbon group having from 2 to 30 carbon atoms and optionally S and/or O atoms bonded to the silicon via an Si—C bond and selected from the group consisting of:
(i) a linear or branched alkyl group comprising from 8 to 30 carbon atoms;
(2i) a linear or branched C$_2$–C$_{20}$ alkenyl group containing one or more double bonds in or at the chain end(s), the said double bonds being optionally conjugated or combined with at least one activating group situated at the α-position;
(3i) an unsaturated aliphatic mono- or bicyclic group containing 5 to 20 cyclic carbon atoms and one or two ethylenic double bond(s) in the ring optionally substituted by one or two linear or branched C$_1$–C$_3$ alkyl group(s), the said cyclic group optionally being bonded to the silicon via a linear or branched C$_2$–C$_{10}$ alkylene radical;
(4i) a mercaptoalkyl group of formula

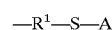 (4i)

wherein:

$R^1$ represents a linear or branched $C_2$–$C_{10}$ alkylene radical, optionally comprising at least one oxygen heteroatom, or an alkylenecycloalkylene radical in which the alkylene part has the same definition as the one given immediately above and the cyclic part contains 5 to 10 carbon atoms and is optionally substituted by one or two linear or branched $C_1$–$C_3$ alkyl group(s); and A is hydrogen or a masking group M bonded to S via a labile bond;

(5i) a polysulphide corresponding to the following formula:

wherein
x=1 to 6,
$R^2$ having the definition as $R^1$ above, and
$R^3$ is a linear or branched $C_1$–$C_{10}$ alkyl;

(6i) a group containing at least one ring, comprising at least one sulphur atom, and having one of the formulae below;

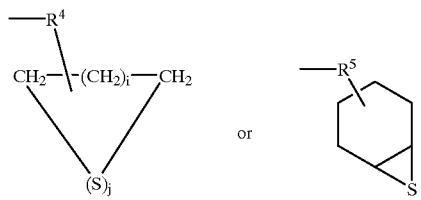

wherein:
i=0, 1 or 2 and j=1 to 6, and
the substituents $R^4$ and $R^5$ are divalent radicals as defined above for $R^1$; and (7i) a sulphoxide group of formula:

 (7i)

wherein the symbols $R^1$ and M have the definitions given above for the formula (4i); and
Z is R or Y;
the sum $m+n+p+q \geq 3$,
$1 \leq m \leq 100$,
$1 \leq n \leq 100$,
$0 \leq p \leq 20$, and
$0 \leq q \leq 40$;
said polyorganosiloxane of formula (IV) being made by the process:
1) reacting a starting polyorganosiloxane of the following formula:

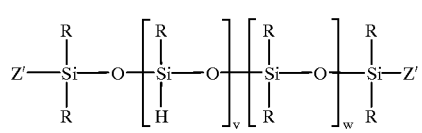 (VI)

wherein:
the R symbols are identical or different and are as defined in formula (IV)

the Z' symbols are identical or different and are R or hydrogen, v is such as v=n+m+q, and w=p; n, m, p and q are as defined in formula (IV), with one or more alcohols of formula YH, wherein Y is methoxy, ethoxy, propoxy or isopropoxy, at a temperature of between 0 and 200° C. in the presence of a dehydrogenation/condensation catalyst wherein only a part of the SiH groups is converted, said alcohol being used as a solvent and as a reactant; and 2) after the dehydrogenation of step 1) has been completed, reacting the residual SiH with an olefinic compound leading to the group W at temperature of between 5 and 100° C. and in the presence of the dehydrogenation/condensation catalyst and in the presence of said alcohol YH being used as a solvent.

2. A process according to claim 1, wherein p=q=0 and $0.1 \leq m/n \leq 5$.

3. A process according to claim 1, wherein W is selected from the group consisting of:
(i) octyl, dodecyl, undecyl or tridecyl group:
(2i) hexenyl or dodecenyl group;
(3i) cyclohexenyl or 1-methylcyclohexenyl optionally bonded to the silicon via a linear or branched $C_2$–$C_6$ alkylene radical;
(4i) a group of the formula:

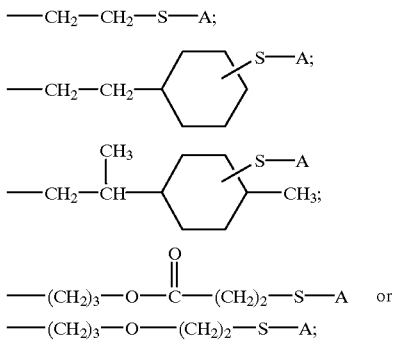

with A=H or M
M being:

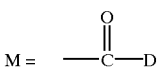

with D being a $C_1$–$C_{12}$ hydrocarbon radical optionally comprising at least one heteroatom;
—$R^6$—$R^7$, with $R^6$ being a linear or branched $C_1$–$C_6$ alkylene and $R^7$ being
a linear or branched $C_1$–$C_4$ alkyl, a linear or branched $C_1$–$C_3$ alkoxy, a phenyl radical, an alkoxysilyl of formula —Si(R')$_k$(OR')$_{3-k}$, where the R' symbols, which are identical or different, are linear or branched $C_1$–$C_3$ alkyl radicals and k=0, 1, 2 or 3 or a group of formula:

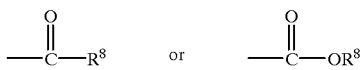

with R[8]=linear or branched $C_1$–$C_3$ alkyl,

M = 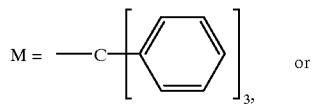 or a radical (7i) of formula:

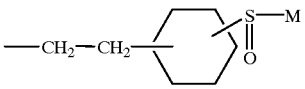

M=—Si(R")$_1$(OR")$_{3-l}$, where the R" symbols, which are identical or different, are linear or branched $C_1$–$C_3$ alkyl and l=0, 1, 2 or 3

(5i) a group of formula:
—(CH$_2$)$_3$—(S)$_4$—(CH$_2$)$_2$—CH$_3$; and (6i) a group of formula:

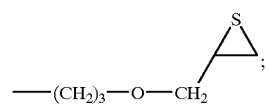 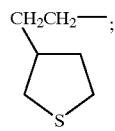

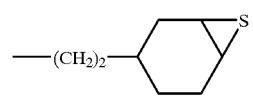 or 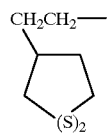

wherein the symbol M represents one of the groups mentioned above with respect to the radical (4i).

4. A process according to claim 1, wherein the catalyst is Pt, Rh, Ru, Pd, or Ni, said catalyst optionally being coupled to a support.

5. A process according to claim 1, wherein the dehydrogenation/condensation of step 1) is carried out at a temperature of between 40 and 70° C.

6. A process according to claim 1, wherein the reaction of step 2) is being catalized by the dehydrogenation/condensation catalyst.

* * * * *